United States Patent
Becker et al.

(10) Patent No.: US 9,061,975 B2
(45) Date of Patent: Jun. 23, 2015

(54) PROCESS FOR PRODUCING PHENOL

(75) Inventors: Christopher L. Becker, Manhattan, KS (US); James R. Lattner, LaPorte, TX (US); Keith H. Kuechler, Friendswood, TX (US); Francisco M. Benitez, Cypress, TX (US); Charles Morris Smith, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 41 days.

(21) Appl. No.: 13/983,989

(22) PCT Filed: Nov. 21, 2011

(86) PCT No.: PCT/US2011/061705
§ 371 (c)(1),
(2), (4) Date: Oct. 28, 2013

(87) PCT Pub. No.: WO2012/118542
PCT Pub. Date: Sep. 7, 2012

(65) Prior Publication Data
US 2015/0038747 A1    Feb. 5, 2015

Related U.S. Application Data (60) Provisional application No. 61/447,170, filed on Feb. 28, 2011.

(30) Foreign Application Priority Data

Apr. 21, 2011    (EP) ..................................... 11163435

(51) Int. Cl.
| | | |
|---|---|---|
| C07C 37/08 | (2006.01) | |
| C07C 37/07 | (2006.01) | |
| C07C 45/51 | (2006.01) | |
| C07C 45/62 | (2006.01) | |
| C07C 37/58 | (2006.01) | |
| C07C 2/74 | (2006.01) | |
| C07C 407/00 | (2006.01) | |
| C07C 45/53 | (2006.01) | |
| C07C 37/055 | (2006.01) | |

(52) U.S. Cl.
CPC ............... *C07C 37/58* (2013.01); *C07C 45/517* (2013.01); *C07C 2/74* (2013.01); *C07C 407/00* (2013.01); *C07C 2101/14* (2013.01); *C07C 2101/16* (2013.01); *C07C 37/07* (2013.01); *C07C 37/08* (2013.01); *C07C 45/53* (2013.01); *C07C 45/62* (2013.01); *C07C 37/055* (2013.01)

(58) Field of Classification Search
None
See application file for complete search history.

(56) References Cited

U.S. PATENT DOCUMENTS

| | | |
|---|---|---|
| 4,439,409 A | 3/1984 | Puppe et al. |
| 4,826,667 A | 5/1989 | Zones et al. |
| 4,954,325 A | 9/1990 | Rubin et al. |
| 5,236,575 A | 8/1993 | Bennett et al. |
| 5,250,277 A | 10/1993 | Kresge et al. |
| 5,292,960 A | 3/1994 | Meier et al. |
| 5,362,697 A | 11/1994 | Fung et al. |
| 6,037,513 A | 3/2000 | Chang et al. |
| 6,049,018 A | 4/2000 | Calabro et al. |
| 6,077,498 A | 6/2000 | Diaz Cabañas et al. |
| 6,201,157 B1 | 3/2001 | Keenan |
| 6,720,462 B2 | 4/2004 | Kuhnle et al. |
| 6,756,030 B1 | 6/2004 | Rohde et al. |
| 7,199,271 B2 | 4/2007 | Fodor |

FOREIGN PATENT DOCUMENTS

| | | | |
|---|---|---|---|
| EP | 0 293 032 | 11/1988 | |
| WO | WO 97/17290 | 5/1997 | |
| WO | WO 2009/025939 | 2/2009 | |
| WO | WO2009/134514 A1 * | 11/2009 | .............. C07C 45/53 |
| WO | WO 2010/024975 | 3/2010 | |
| WO | WO 2011/100013 | 8/2011 | |

\* cited by examiner

*Primary Examiner* — Brian J Davis
(74) *Attorney, Agent, or Firm* — Siwen Chen; Stephen A. Baehl (57) ABSTRACT

In a process for producing phenol, cyclohexylbenzene is oxidized to form a first reaction product comprising cyclohexylbenzene hydroperoxide and at least a portion of the cyclohexylbenzene hydroperoxide is then cleaved to form a second reaction product comprising phenol and cyclohexanone. At least one of the first and second reaction products comprises cyclohexenone, which is hydrogenated to produce further cyclohexanone.

21 Claims, 1 Drawing Sheet

PROCESS FOR PRODUCING PHENOL

PRIORITY CLAIM

This application is a National Stage Application of International Application No. PCT/US2011/061705 filed Nov. 21, 2011, which claims priority to U.S. Provisional Application Ser. No. 61/447,170 filed Feb. 28, 2011, and European Application No. 11163435.8 filed Apr. 21, 2011, the disclosures of which are fully incorporated herein by their reference.

CROSS REFERENCE TO RELATED APPLICATIONS

This application is related to International Patent Cooperation Treaty Application No. PCT/US2010/057753 filed Nov. 23, 2010.

FIELD

The present invention relates to a process for producing phenol.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process via cumene. This is a three-step process involving alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the cost of propylene is likely to increase, due to a developing shortage of propylene. Thus, a process that does not require propylene as a feed and coproduces higher ketones, rather than acetone, may be an attractive alternative route to the production of phenol.

One such process involves the catalytic hydroalkylation of benzene to produce cyclohexylbenzene, followed by the oxidation of the cyclohexylbenzene (analogous to cumene oxidation) to cyclohexylbenzene hydroperoxide, which is then cleaved to produce phenol and cyclohexanone in substantially equimolar amounts. Such a process is described in, for example, U.S. Pat. No. 6,037,513, in which the hydroalkylation catalyst is a bifunctional catalyst comprising at least one hydrogenation metal and a molecular sieve of the MCM-22 family.

However, one problem in producing phenol via cyclohexylbenzene is that the oxidation and cleavage processes produce significant quantities of impurities, such as cyclohexenone, in addition to the desired products. Cyclohexenone is a particularly troublesome impurity since it acts substantially like cyclohexanone in the fractionation systems conventionally employed to separate the product mixtures into individual components. As a result the cyclohexenone tends to concentrate in the cyclohexanone product.

Existing methods of removing cyclohexenone from product streams containing cyclohexanone normally involve reacting the cyclohexenone with other components in the product stream, such as cyclohexanone, to produce heavies which can be removed by fractionation. However, these processes reduce the yield of the desired cyclohexanone and also potentially require additional distillation equipment.

There is therefore a need for an improved method for removing cyclohexenone from the product streams produced in the oxidation of cyclohexylbenzene and the cleavage of cyclohexylbenzene hydroperoxide. It has now been found that, because cyclohexenone has two double bonds in a conjugated system, its olefinic double bond is substantially more reactive than the single ketone double bond in cyclohexanone. This difference in reactivity is utilized, in accordance with the invention, to selectively hydrogenate cyclohexenone to cyclohexanone with minimal yield loss of the cyclohexanone.

U.S. Pat. No. 5,292,960 discloses a process for the purification of cyclohexanone which has been obtained by dehydrogenation of a cyclohexanone/cyclohexanol mixture, wherein the dehydrogenation mixture is treated in the gas or liquid phase with $H_2$ on a hydrogenation catalyst at 20° C. to 180° C. and at an $H_2$ pressure of 0.1 to 15 bar. The cyclohexanone/cyclohexanol mixture employed in the '960 patent is obtained either by oxidation of cyclohexane or by hydrogenation of phenol. In either event, the impurities removed in the purification process are said to be "not completely known" (column 1, lines 29 and 30).

U.S. Pat. No. 7,199,271 discloses a method for reducing the concentration of cyclohexenone in an organic mixture comprising cyclohexenone, particularly a mixture of cyclohexanol and cyclohexenone produced by oxidizing cyclohexane. The method comprises treating the organic mixture with an effective amount of additive comprising at least one of sulfurous acid, a salt of sulfurous acid, or an alkali hydroxide.

SUMMARY

In one aspect, the invention resides in a process for producing phenol, the process comprising:

(a) oxidizing cyclohexylbenzene to form a first reaction product comprising cyclohexylbenzene hydroperoxide; and (b) cleaving at least a portion of the cyclohexylbenzene hydroperoxide from (a) to form a second reaction product comprising phenol and cyclohexanone, wherein at least one of the first and second reaction products comprises cyclohexenone and the process further comprises:

(c) hydrogenating at least a portion of the cyclohexenone to cyclohexanone.

Conveniently, the hydrogenation conditions comprise a temperature of about 20° C. to about 150° C., such as about 60° C. to about 100° C. and a hydrogen partial pressure of about 0 kPag to about 2000 kPag, such as about 200 kPag to about 1000 kPag.

Conveniently, the hydrogenation catalyst comprises a hydrogenation component and a support.

In one embodiment, the hydrogenation component comprises at least one element or compound thereof selected from Groups 6 to 10 of the Periodic Table of Elements, such as palladium or a palladium compound, and is present in an amount from about 0.1 to about 10 wt %, such as about 0.3 to about 1 wt %, of the hydrogenation catalyst.

In one embodiment, the support comprises at least one of aluminum oxide, silica, silicate, aluminosilicate, carbon, and a carbon nanotube.

Conveniently, at least part of the second reaction product comprising phenol, cyclohexanone, and cyclohexenone is subjected to the hydrogenating (c).

In one embodiment, the second reaction product is separated into a first stream rich in cyclohexanone and cyclohexenone and a second stream rich in phenol, and at least part of the first stream is subjected to the hydrogenating (c).

Conveniently, at least part of the cyclohexylbenzene in (a) is formed by reacting benzene with hydrogen.

Conveniently, the process further comprises dehydrogenating at least a part of the cyclohexanone from the second reaction product to form phenol.

DETAILED DESCRIPTION OF THE EMBODIMENTS

Described herein is a process for producing phenol by oxidizing cyclohexylbenzene to form a first reaction product comprising cyclohexylbenzene hydroperoxide and then cleaving at least a portion of the cyclohexylbenzene hydroperoxide to form a second reaction product comprising phenol and cyclohexanone. One or both of the first and second reaction products contain cyclohexenone as an impurity, which is difficult to separate from the desired cyclohexanone by conventional distillation methods. Thus the present process employs selective hydrogenation to convert at least part of the cyclohexenone in the first and/or second reaction products to cyclohexanone. The selective hydrogenation process is accompanied by only minimal yield loss of the desired cyclohexanone.

Production of Cyclohexylbenzene

Any known technique can be used to produce the cyclohexylbenzene (CHB) employed in the present process, including direct alkylation of benzene with cyclohexene in the presence of an acid catalyst, such as zeolite beta or an MCM-22 family molecular sieve, or oxidative coupling of benzene to biphenyl followed by hydrogenation of the biphenyl. However, in practice, the cyclohexylbenzene is generally produced by contacting benzene with hydrogen under hydroalkylation conditions in the presence of a hydroalkylation catalyst whereby the benzene undergoes the following reaction (1) to produce cyclohexylbenzene (CHB):

(1)

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa. Suitable values for the molar ratio of hydrogen to benzene are between about 0.15:1 and about 15:1, such as between about 0.4:1 and about 4:1, for example, between about 0.4 and about 0.9:1.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49; (b) MCM-56; and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with themolecular sieve. Typically, the catalyst composite is produced by co-pelletization, in which a mixture of the molecular sieve and the metal-containing inorganic oxide are formed into pellets at high pressure (generally about 350 to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions, such as silica-alumina-thoria, silica-alumina-zirconia, silica-alumina-magnesia, and silica-magnesia-zirconia.

Although the hydroalkylation step is highly selective towards cyclohexylbenzene, the effluent from the hydroalkylation reaction will normally contain some dialkylated products, as well as unreacted aromatic feed and the desired monoalkylated species. The unreacted aromatic feed is normally recovered by distillation and recycled to the alkylation reactor. The bottoms from the benzene distillation are further distilled to separate the monocyclohexylbenzene product from any dicyclohexylbenzene and other heavies. Depending on the amount of dicyclohexylbenzene present in the reaction effluent, it may be desirable to transalkylate the dicyclohexylbenzene with additional benzene to maximize the production of the desired monoalkylated species.

Although the hydroalkylation reaction using an MCM-22 family zeolite catalyst activated by the process described herein is highly selective towards cyclohexylbenzene, the effluent from the hydroalkylation reaction will inevitably contain some dicyclohexylbenzene by-product. Depending on the amount of this dicyclohexylbenzene, it may be desirable to either (a) transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,049,018), zeolite Y and mordenite. The transalkylation reaction is typically conducted under at least partial liquid phase conditions, which suitably include a temperature of about 100° C. to about 300° C., a pressure of about 800 to about 3500 kPa, a weight hourly space velocity of about 1 to about 10 $hr^{-1}$ on total feed, and a benzene/dicyclohexylbenzene weight ratio about of 1:1 to about 5:1.

Dealkylation or cracking is also typically effected in a reactor separate from the hydroalkylation reactor, such as a reactive distillation unit, at a temperature of about 150° C. to about 500° C. and a pressure of 15 to 500 psig (200 to 3550 kPa) over an acid catalyst, such as an aluminosilicate, an aluminophosphate, a silicoaluminphosphate, amorphous silica-alumina, an acidic clay, a mixed metal oxide, such as $WO_x/ZrO_2$, phosphoric acid, sulfated zirconia and mixtures thereof. Generally, the acid catalyst includes at least one aluminosilicate, aluminophosphate, or silicoaluminphosphate of the FAU, AEL, AFI and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is typically is from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least part of the cyclohexane in the $C_6$-rich stream portion to benzene, which again can be recycled to the hydroalkylation reaction. The dehydrogenation catalyst generally comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium and compounds and mixtures thereof. Typically, the hydrogenation-dehydrogenation component is present in an amount between about 0.1 and about 10 wt % of the catalyst. A suitable inorganic promoter (c) comprises at least one metal or compound thereof selected from Group 1 of the Periodic Table of Elements, such as a potassium compound. Typically, the promoter is present in an amount between about 0.1 and about 5 wt % of the catalyst. Suitable dehydrogenation conditions include a temperature of about 250° C. to about 500° C., a pressure of about atmospheric to about 500 psig (100 to 3550 kPa), a weight hourly space velocity of about 0.2 to 50 hr$^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{12}$ stream. Similarly, bicyclohexyl (BCH) can lead to separation problems downstream. Thus, at least part of the hydroalkylation reaction product may be treated with a catalyst under conditions to remove at least 1,1-methylcyclopentylbenzene and/or bicyclohexyl from the product. The catalyst is generally an acid catalyst, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

The catalytic treatment can be conducted on the direct product of the hydroalkylation reaction or after distillation of the hydroalkylation reaction product to separate the $C_6$ and/or the heavies fraction.

The cyclohexylbenzene product from the hydroalkylation reaction and any downstream reaction to remove the impurities discussed above is separated from the reaction effluent(s) and is fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide. This is accomplished by contacting the cyclohexylbenzene with an oxygen-containing gas, such as air and various derivatives of air. For example, it is possible to use air that has been compressed and filtered to removed particulates, air that has been compressed and cooled to condense and remove water, or air that has been enriched in oxygen above the natural approximately 21 mol % in air through membrane enrichment of air, cryogenic separation of air or other conventional means.

The oxidation is conducted in the presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide may be used. Preferably, the catalyst is N-hydroxyphthalimide. Another suitable catalyst is N,N',N"-thihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N', N"-trihydroxyisocyanuric acid is employed in an amount between 0.0001 wt % to 15 wt %, such as between 0.001 to 5 wt %, of the cyclohexylbenzene.

Suitable conditions for the oxidation step include a temperature between about 70° C. and about 200° C., such as about 90° C. to about 130° C., and a pressure of about 50 to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Typically, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation reaction effluent. Generally, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent. The oxidation reaction effluent may further comprise imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

At least a portion of the oxidation reaction effluent is subjected to a cleavage reaction to convert the cyclohexyl-1-phenyl-1-hydroperoxide to phenol and cyclohexanone. Cleavage may be conducted on oxidation reaction effluent, with or without the effluent undergoing any prior separation or treatment. For example, all or a fraction of the oxidation reaction effluent may be subjected to high vacuum distillation to generate a product enriched in unreacted cyclohexylbenzene and leave a residue which is concentrated in the desired cyclohexyl-1-phenyl-1-hydroperoxide and which is subjected to the cleavage reaction. In general, however, such concentration of the cyclohexyl-1-phenyl-1-hydroperoxide is neither necessary nor preferred. Additionally or alternatively, all or a fraction of the oxidation effluent, or all or a fraction of the vacuum distillation residue may be cooled to cause crystallization of the unreacted imide oxidation catalyst, which can then be separated either by filtration or by scraping from a heat exchanger surface used to effect the crystallization. At least a portion of the resultant oxidation composition reduced or free from imide oxidation catalyst may be subjected to the cleavage reaction.

As another example, all or a fraction of the oxidation effluent may be subjected to water washing and then passage through an adsorbent, such as a 3A molecular sieve, to separate water and other adsorbable compounds, and provide an oxidation composition with reduced water or imide content that may be subjected to the cleavage reaction. Similarly, all or a fraction of the oxidation effluent may undergo a chemically or physically based adsorption, such as passage over a bed of sodium carbonate to remove the imide oxidation catalyst (e.g., NHPI) or other adsorbable components, and provide an oxidation composition reduced in oxidation catalyst or other adsorbable component content that may be subjected to the cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in International Application No. WO 2009/025939.

Hydroperoxide Cleavage

The final reactive step in the conversion of the cyclohexylbenzene into phenol and cyclohexanone involves the acid-catalyzed cleavage of the cyclohexyl-1-phenyl-1-hydroperoxide produced in the oxidation step.

Generally, the acid catalyst used in the cleavage reaction is at least partially soluble in the cleavage reaction mixture, is stable at a temperature of at least 185° C. and has a lower volatility (higher normal boiling point) than cyclohexylbenzene. Typically, the acid catalyst is also at least partially soluble in the cleavage reaction product. Suitable acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide and sulfur trioxide. Sulfuric acid is a preferred acid catalyst.

In various embodiments, the cleavage reaction mixture contains at least 50 weight-parts-per-million (wppm) and no greater than 5000 wppm of the acid catalyst, or at least 100 wppm to and to no greater than 3000 wppm, or at least 150 wppm to and no greater than 2000 wppm of the acid catalyst, or at least 300 wppm and no greater than 1500 wppm of the acid catalyst, based upon total weight of the cleavage reaction mixture.

In one embodiment, the cleavage reaction mixture contains a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less, such as acetone, methylethyl ketone, 2- or 3-pentanone, cyclohexanone, and methylcyclopentanone. The preferred polar solvent is acetone. Generally, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

In various embodiments, the cleavage reaction mixture includes cyclohexylbenzene in an amount of at least 50 wt %, or at least 60 wt %, or at least 65 wt %, or at least 70 wt %, or at least 80 wt %, or at least 90 wt %, based upon total weight of the cleavage reaction mixture.

Suitable cleavage conditions include a temperature of greater than 50° C. and no greater than 200° C., or at least 55° C. and no greater than 120° C., and a pressure of at least 1 and no greater than 370 psig (at least 7 and no greater than 2,550 kPa, gauge), or at least 14.5 and no greater than 145 psig (at least 100 and no greater than 1,000 kPa, gauge) such that the cleavage reaction mixture is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

The major products of the cleavage reaction of cyclohexyl-1-phenyl-1-hydroperoxide are phenol and cyclohexanone, each of which generally comprise about 40 to about 60 wt %, or about 45 to about 55 wt % of the cleavage reaction product, such wt % based on the weight of the cleavage reaction product exclusive of unreacted cyclohexylbenzene and acid catalyst.

The cleavage reaction product also typically contains unreacted acid catalyst and hence at least a portion of the cleavage reaction product is normally neutralized with a basic material to remove or reduce the level of acid in the product.

Suitable basic materials include alkali metal hydroxides and oxides, alkali earth metal hydroxides and oxides, such as sodium hydroxide, potassium hydroxide, magnesium hydroxide, calcium hydroxide, calcium oxide and barium hydroxide. Sodium and potassium carbonates may also be used, optionally at elevated temperatures.

In various embodiments, the basic material comprises one or more of: a caustic exchange resin (e.g., sulfonic ion-exchange resin); ammonia or ammonium hydroxide; a basic clay such as limestone, dolomite, magnesite, sepiolite, and olivine; an activated carbon and/or impregnated activated carbon; an anionic exchange resin, such as a weakly basic ion exchange resin having a styrene-divinyl benzene polymer backbone and an amine functional structure selected from —N(CH$_3$)$_2$, —NRH or —NR$_2$, where R is a hydrogen or an alkyl group containing 1 to 20 carbon atoms; an amine polysiloxane functionalized with ethylenediamine; an organic basic material grafted on microporous or mesoporous metal oxides; other organo-inorganic solids, such as zeolites exchanged with a metal selected from the group of lithium, sodium potassium, rubidium, cesium, calcium, barium, strontium, and radium; an oxide of Group III of the Periodic Table of Elements treated with a metal selected from lithium, potassium, sodium, rubidium, and cesium; a supported or solid alkali, alkaline-earth metal or organometallic; a magnesium silicate generally derived from the interaction of a magnesium salt and soluble silicate; a salt with basic hydrolysis, such as sodium acetate, sodium bicarbonate, sodium phenate, and sodium carbonate; and amine(s), such as a primary, secondary, or tertiary aliphatic amines or aromatic amines, e.g., anilines, n-butyl amine, heterocyclic amines, such as pyridines, piperidines, piperazines, tri-ethyl amine, aliphatic or aromatic diamines, and alkanolamines. In particular, amines in the form of their salts with weak organic acids may be used. Conveniently, the basic material is a diamine, such as 2-methylpentamethylenediamine or hexamethylenediamine, which are commercially available from Invista S.à r.l. Corporation under the trade designations DYTEK™ A and DYTEK™ HMD.

Suitable solid basic materials include: basic metal oxide families; alkali on metal oxides; alkaline-earth on metal oxides; alkali and alkaline-earth zeolites; transition metals, rare earth and higher valency oxides; hydrotalcites, calcined hydrotalcites and spinels, specifically hydrotalcites treated with an alkali metal selected from lithium, potassium, sodium, rubidium, cesium, and combinations thereof; perovskites; and beta-aluminas.

In one embodiment, the basic material is one or more of the hindered amines described in U.S. Pat. No. 6,201,157. It will be understood that the basic material may be added in the anhydrous state or may be an aqueous solution of any of the foregoing basic materials, particularly the metal hydroxides and salts with basic hydrolysis.

Conveniently, a liquid basic material employed a neutralization reaction in the present invention, such as an amine or diamine as has been discussed, has a relatively low volatility, with a normal boiling point temperature above that of cyclohexylbenzene, such that it will tend to remain in the bottoms product in subsequent fractionation operations that may be conducted on the least a portion of the treated cleavage reaction product that may contain such liquid basic material.

The conditions at which the neutralization reaction is effected vary with the acid catalyst and basic material employed. Suitable neutralization conditions include a temperature of at least 30° C., or at least 40° C., or at least 50° C., or at least 60° C., or at least 70° C., or at least 80° C., or at least 90° C. Other suitable neutralization conditions include a temperature of no greater than 200° C., or no greater than 190° C., or no greater than 180° C., or no greater than 170° C., or no greater than 160° C., or no greater than 150° C., or no greater than 140° C., or no greater than 130° C., or no greater than 120° C., or no greater than 110° C., or no greater than 100° C. In various embodiments, the neutralization conditions include a temperature that is reduced from cleavage reaction conditions, for example, the temperature may be 1° C., or 5° C., or 10° C., or 15° C., or 20° C., or 30° C., or 40° C. lower than the temperature of the cleavage reaction.

Suitable neutralization conditions may include a pressure of about 1 to about 500 psig (5 kPa to 3450 kPa, gauge), or about 10 to 200 psig (70 to 1380 kPa, gauge) such that the treated cleavage reaction mixture is completely or predominantly in the liquid phase during the neutralization reaction.

After neutralization, the neutralized acid product can be removed from the cleavage product leaving a crude mixture of phenol and cyclohexanone which is then treated to recover the phenol and/or cyclohexanone products.

Selective Hydrogenation of Cyclohexenone Impurity

One of the undesirable impurities produced during the cyclohexylbenzene oxidation step and more particularly during the cyclohexylbenzene hydroperoxide cleavage step is cyclohexenone. In particular, cyclohexenone acts substantially like cyclohexanone in the fractionation systems conventionally employed to separate the desired phenol and cyclohexanone from the effluent of the cleavage reaction. Thus, if not removed, the cyclohexenone tends to concentrate in the cyclohexanone product.

Accordingly, in the present process, at least part of the product of the cyclohexylbenzene oxidation step and/or the cyclohexylbenzene hydroperoxide cleavage step is subjected to a selective hydrogenation process to convert at least part of the cyclohexenone impurity to cyclohexanone. Generally, the selective hydrogenation process is effected on the product of the cyclohexylbenzene hydroperoxide cleavage step, either before or after separation of the phenol from the cyclohexanone and cyclohexenone-containing portion of the cleavage product. In various embodiments, the product of the cleavage and/or oxidation reactions contains at least 0.001 wt % of the cyclohexenone impurity, or at least 0.005, or at least 0.1, or at least 0.05, or at least 0.07, or at least 0.1, or at least 0.5 wt % of the cyclohexenone impurity. Typically, the cleavage product contains from about 0.001 to about 1 wt % of cyclohexenone impurity. In some embodiments, the oxidation and/or cleavage reaction product contains up to 10 wt % of the cyclohexenone impurity. The wt % is based upon total weight of the product.

The selective hydrogenation process may be conducted in the presence of a hydrogenation catalyst and under conditions which are effective to selectively hydrogenate the olefinic group in the cyclohexenone but which are substantially inert to the ketone group in the cyclohexanone and the aromatic ring in the phenol. A suitable catalyst comprises a hydrogenation component provided on a support. A suitable hydrogenation component comprises at least one element or compound thereof selected from Groups 6 to 10 of the Periodic Table of Elements, such as palladium or a palladium compound, whereas a suitable support comprises at least one of aluminum oxide, silica, silicate, aluminosilicate, carbon, and a carbon nanotube. Typically, the hydrogenation component comprises about 0.1 wt % to about 10 wt %, such as about 0.3 wt % to about 1 wt % of the hydrogenation catalyst.

Suitable conditions for the selective hydrogenation process comprise a temperature of about 20° C. to about 150° C., such as about 60° C. to about 100° C., and a hydrogen partial pressure of about 0 kPag to about 2000 kPag, such as about 200 kPag to about 1000 kPag. The reaction can be carried out in the gas or liquid phase or in a mixed gas/liquid phase.

In various embodiments, at least 50%, or at least 60%, or at least 70%, or at least 80%, or at least 90%, or substantially all of the cyclohexenone is hydrogenated to cyclohexanone.

As discussed below, the selective hydrogenation process can be conducted on the entire $C_6$ oxygenate portion of the cleavage effluent or at least part of the phenol may be removed from the cleavage effluent before the latter is subjected to selective hydrogenation.

In various embodiments, the cleavage reaction product comprising phenol, cyclohexanone, and cyclohexenone is separated into a first stream rich in cyclohexanone and cyclohexenone and a second stream rich in phenol, and at least part of the first stream is subjected to hydrogenation. When a stream is described as being "rich in" in a specified species (e.g., rich in cyclohexanone), it is meant that the wt % of the specified species in that stream is enriched relative to the feed stream (i.e., input).

Cyclohexanone Dehydrogenation

In order to maximize the production of phenol from the benzene starting material, at least part of the cyclohexanone produced by the cleavage and subsequent hydrogenation process may be subjected to dehydrogenation according to the following reaction (2):

(2)

Cyclohexanone and phenol produce an azeotropic mixture composed of 28 wt % cyclohexanone and 72 wt % phenol, so that any attempt to separate the phenol and cyclohexanone from the effluent of the cyclohexylbenzene hydroperoxide cleavage step by simple distillation results in this azeotropic mixture. Moreover, although the efficiency of the separation can be enhanced by conducting the distillation under at least partial vacuum, phenol/cyclohexanone separation remains a costly process. Thus, in one embodiment, the feed to the optional dehydrogenation step has the same phenol/cyclohexanone ratio as the cleavage effluent, thereby avoiding the need for an initial expensive separation step. Depending on the efficiency of the cyclohexanone dehydrogenation, the final product may contain substantially all phenol, thereby at least reducing the problem of separating the phenol from the cleavage effluent.

In another embodiment, the cleavage effluent is subjected to one or more separation processes to recover or remove one or more components of the effluent prior to dehydrogenation. In particular, the cleavage effluent is conveniently subjected to at least a first separation step to recover some or all of the phenol from the effluent, typically so that the effluent stream fed to the dehydrogenation reaction contains less than 50 wt %, for example less than 30 wt %, such as less than 1 wt %, phenol. The separation of phenol is conveniently effected by vacuum. Additional distillation steps can be used to remove components boiling below 155° C. (as measured at 101 kPa), such as benzene and cyclohexene, and/or components boiling above 185° C. (as measured at 101 kPa), such as 2-phenyl phenol and diphenyl ether, prior to feeding the effluent stream to the dehydrogenation reaction.

The catalyst employed in the cyclohexanone dehydrogenation reaction comprises (i) a support; (ii) a dehydrogenation component comprising at least one metal or compound thereof selected from Groups 6 to 10 of the Periodic Table of Elements; and (iii) potassium or a potassium compound.

The catalyst support is typically formed of silica, a silicate, an aluminosilicate, carbon, or carbon nanotubes. In one embodiment, the support comprises a crystalline, mesoporous silicate material selected from MCM-41, MCM-48, and MCM-50. In other embodiments, the silica support has a surface area as measured by ASTM D3663 in the range from about 10 $m^2$/gram to about 1000 $m^2$/gram, such as from about 20 $m^2$/gram to about 500 $m^2$/gram, a pore volume in the range of from about 0.2 cc/gram to about 3.0 cc/gram and a median pore diameter in the range from about 10 angstroms to about 2000 angstroms, such as from about 20 angstroms to about 500 angstroms. Such pore volume and median pore diameter values are determined by mercury intrusion porosimetry as described in ASTM D4284. The support may or may not comprise a binder.

Generally, the dehydrogenation component comprises at least one metal component selected from Groups 6 to 10 of the Periodic Table of Elements, such as platinum and palladium. Typically, the dehydrogenation component is present in an amount between about 0.1 wt % and about 10 wt % of the catalyst. In one embodiment, the dehydrogenation component is present in an amount between about 0.1 wt % and about 5 wt % of the catalyst, or between about 0.2 wt % and about 4 wt % of the catalyst, or between about 0.3 wt % and about 3 wt % of the catalyst, or between about 0.4 wt % and 2 wt % of the catalyst.

In order to achieve optimal phenol selectivity together with enhanced stability of the dehydrogenation metal, the dehydrogenation catalyst contains potassium or a potassium compound in an amount of about 0.15 to about 0.6 wt %, typically about 0.2 to about 0.5 wt %, of metallic potassium based upon the total weight of the catalyst composition.

The dehydrogenation catalyst is typically prepared by sequentially or simultaneously treating the support, such as by impregnation, with one or more liquid compositions comprising the dehydrogenation component or a precursor thereof, the tin component or a precursor thereof and/or the optional inorganic base component or a precursor in a liquid carrier, such as water. An organic dispersant may be added to each liquid carrier to assist in uniform application of the metal component(s) to the support. Suitable organic dispersants include amino alcohols and amino acids, such as arginine.

Generally, the organic dispersant is present in the liquid composition in an amount between about 1 and about 20 wt % of the liquid composition.

In one preferred embodiment, the catalyst is prepared by sequential impregnation with the potassium component being applied to the support before the dehydrogenation component.

After application of each of the dehydrogenation metal and the potassium to the support, the support is preferably heated at a temperature of about 100° C. to about 700° C. for example about 200° C. to about 500° C., such as 300° C. to about 450° C., for a time of about 0.5 to about 50 hours, such as about 1 to about 10 hours. In addition to removing any liquid carrier and dispersant used to apply the metal component to the support, the heating is believed to assist in bonding the metal to the support and thereby improve the stability of the final catalyst. The heating is preferably conducted in an oxidizing atmosphere, such as air, although a reducing atmosphere, such as hydrogen, can also be employed.

In one embodiment, the dehydrogenation catalyst has an oxygen chemisorption value of greater than about 30%, such as greater than about 40%, for example greater than about 50%, even greater than about 60%, greater than about 70%, or even greater than about 80%. As used herein, the oxygen chemisorption value of a particular catalyst is a measure of metal dispersion on the catalyst and is defined as [the ratio of the number of moles of atomic oxygen sorbed by the catalyst to the number of moles of dehydrogenation metal contained by the catalyst]×100%. The oxygen chemisorption values referred to herein are measured using the following technique. Chemisorption measurements are obtained under static high vacuum conditions on a Quantachrome Autosorb 1A instrument. Approximately 0.3-0.5 grams of catalyst are loaded into a quartz cell and dried in flowing He by heating at 4° C./min to 130° C. and holding for 1 hour. The flow is then switched to hydrogen and the catalyst is reduced in flowing hydrogen by heating at 2° C./min to 425° C., holding isothermal for 2 hours, and then cooling to 400° C. in flowing hydrogen. Following reduction, the sample is evacuated (while still at 400° C.) with a turbomolecular pump for 30 minutes to remove any chemisorbed hydrogen. With the sample still under vacuum, the temperature is lowered to 40° C. and held isothermal during subsequent experiments. An 8-point isotherm (with pressures between 80 and 400 torr [11 kPa to 53 kPa]) is measured at 40° C. with $O_2$ as the adsorbent molecule. Extrapolation of the linear portion of this curve to zero pressure gives the total or combined adsorption uptake.

Suitable conditions for the dehydrogenation step comprise a temperature of about 250° C. to about 750° C., a pressure of about 0.01 atm to about 500 psig (1 to 3450 kPag), and a weight hourly space velocity (WHSV) of about 2 to 50 $hr^{-1}$, for example a temperature of about 250° C. to about 500° C. and a pressure of about 100 kPa to about 2000 kPa, such as a temperature of about 300° C. to about 450° C. and a pressure of about 100 kPa to 300 kPa. To improve catalyst stability and assist in extracting the hydrogen generated in the dehydrogenation reaction, hydrogen may be cofed to the dehydrogenation reaction, typically such that the molar ratio of hydrogen to cyclohexanone in the dehydrogenation feed is about 0:1 to about 20:1.

The reactor configuration used for the dehydrogenation process generally comprises one or more fixed bed reactors containing the dehydrogenation catalyst. Provision can be made for the endothermic heat of reaction, preferably by multiple adiabatic beds with interstage heat exchangers. The temperature of the reaction stream drops across each catalyst bed, and then is raised by the heat exchangers. Preferably, 3 to 5 beds are used, with a temperature drop of about 30° C. to about 100° C. across each bed. Preferably the last bed in the series runs at a higher exit temperature than the first bed in the series.

The effluent from the cyclohexanone dehydrogenation reaction is composed mainly of phenol and hydrogen. The desired phenol is easily removed from the reaction effluent by fractionation to leave a hydrogen stream which, after suitable purification, can be recycled to the benzene hydroalkylation step.

By employing the present dehydrogenation process, substantially all the cyclohexanone in the cyclohexylbenzene hydroperoxide cleavage effluent can be converted to phenol. In practice, however, depending on market conditions, there is likely to be a significant demand for cyclohexanone product. This can be readily met using the present process by reliance on the reversible nature of the reaction (2), namely by hydrogenating at least some of the phenol back to cyclohexanone. This can readily be achieved by, for example, contacting the phenol with hydrogen in the presence of a hydrogenation catalyst, such as platinum or palladium, under conditions including a temperature of about 20° C. to about 250° C., a pressure of about 101 kPa to about 10000 kPa and a hydrogen to phenol molar ratio of about 1:1 to about 100:1.

Figure 1:
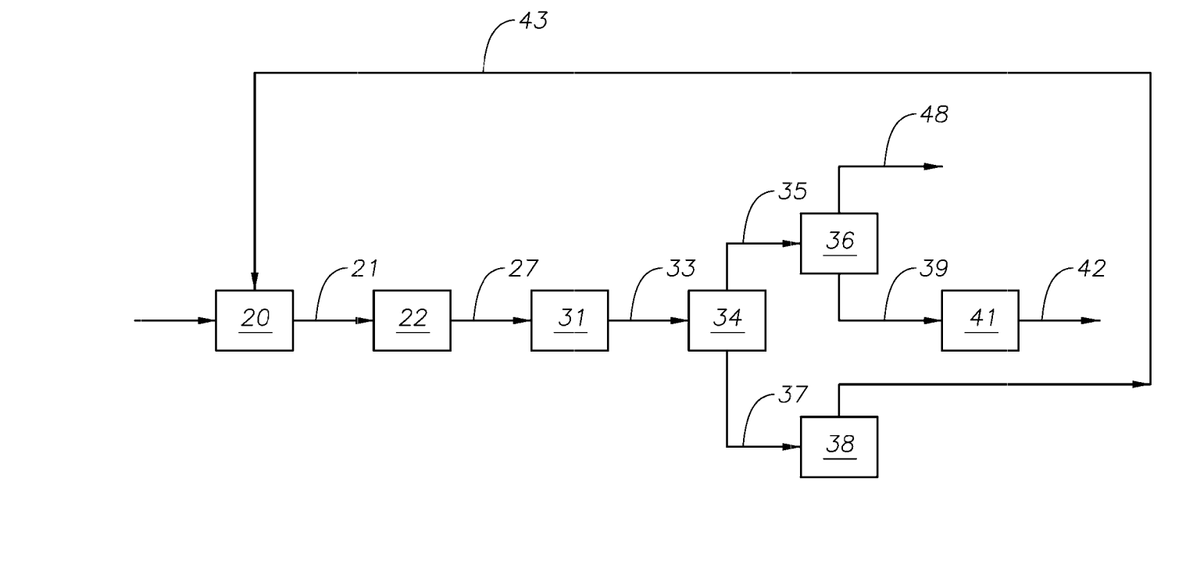
FIG. 1 is a flow diagram of a process of producing phenol from cyclohexylbenzene according to a first example of the invention.

The invention will now be more particularly described with reference to the accompanying drawing.

FIG. 1 illustrates a process for producing phenol from benzene in which the benzene is initially subjected to hydroalkyation to produce cyclohexylbenzene (not shown). The cyclohexylbenzene is oxidized to the hydroperoxide, which is then cleaved to produce phenol and cyclohexanone and the entire cyclic $C_6$ oxygenate portion of cleavage effluent is subjected to hydrogenation to remove cyclohexenone by-product in the cleavage effluent. In the process shown in FIG. 1, product of the hydroalkyation reaction, which contains phenyl cyclohexene in addition to the desired cyclohexylbenzene, is initially mixed with hydrogen and passed to a hydrogenation reactor 20, where the phenyl cyclohexene is hydrogenated to produce additional cyclohexylbenzene. The effluent from the hydrogenation reactor 20 is supplied via line 21 to an oxidation reaction zone 22.

The cyclohexylbenzene is then oxidized to cyclohexylbenzene hydroperoxide in the oxidation zone 22 to produce an oxidation effluent which is fed by line 27 to cleavage reaction zone 31 where it is converted to phenol and cyclohexanone before being fed via line 33 to primary fractionator 34. Primary fractionator 34 divides the cleavage effluent into a light fraction and a heavy fraction. The light fraction contains the desired phenol and cyclohexanone, together with $C_{12}$- impurities, such as methylcyclopentanone and cyclohexenone. The heavy fraction contains unreacted cyclohexylbenzene and any $C_{12}$+ impurities. The light fraction exits the fractionator 34 as overhead and is passed by line 35 to a secondary fractionator 36, whereas the heavy fraction leaves the fractionator 34 as a bottoms stream and is fed by line 37 to a further fractionator 38.

The secondary fractionator 36 removes methylcyclopentanone from the light fraction of the cleavage effluent via line 48 before the remainder is fed by line 39 to a hydrogenation reactor 41. The cyclohexenone in the cleavage effluent is selectively hydrogenated to cyclohexanone in the reactor 41 to produce a product stream 42 which is rich in phenol and cyclohexanone and substantially free of cyclohexenone.

Fractionator 38 removes $C_{12}$+ impurities from the heavy fraction of the cleavage effluent so that these can be purged or subjected to further treatment. The overhead from fractionator 38 is rich in unreacted cyclohexylbenzene and is recycled via line 43 to the hydrogenation reactor 20.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing phenol, the process comprising:
   (a) oxidizing cyclohexylbenzene to form a first reaction product comprising cyclohexylbenzene hydroperoxide; and
   (b) cleaving at least a portion of the cyclohexylbenzene hydroperoxide from (a) to form a second reaction product comprising phenol and cyclohexanone,
   wherein at least one of the first reaction product and the second reaction product comprises cyclohexenone and the process further comprises:
   (c) hydrogenating at least a portion of the cyclohexenone to cyclohexanone.

2. The process of claim 1, wherein at least one of the first and second reaction products comprises at least 0.01 wt % of cyclohexenone, based upon total weight of the reaction product.

3. The process of claim 1, wherein at least one of the first and second reaction products comprises at least 0.05 wt % of cyclohexenone, based upon total weight of the reaction product.

4. The process of claim 1, wherein the hydrogenating (c) is conducted to a degree sufficient to hydrogenate at least 70% of the cyclohexenone to cyclohexanone.

5. The process of claim 1, wherein the hydrogenating (c) is conducted to a degree sufficient to hydrogenate at least 90% of the cyclohexenone to cyclohexanone.

6. The process of claim 1, wherein at least one of the first and the second reaction products comprises up to 10 wt % of cyclohexenone, based upon total weight of the reaction product.

7. The process of claim 1, wherein the hydrogenating (c) is conducted at hydrogenation conditions comprising a temperature of about 20° C. to about 150° C.

8. The process of claim 1, wherein the hydrogenating (c) is conducted at hydrogenation conditions comprising a temperature of about 60° C. to about 100° C.

9. The process of claim 1, wherein the hydrogenating (c) is conducted at hydrogenation conditions comprising a hydrogen partial pressure of about 0 kPag to about 2000 kPag.

10. The process of claim 1, wherein the hydrogenating (c) is conducted at hydrogenation conditions comprising a hydrogen partial pressure of about 200 kPag to 1000 kPag.

11. The process of claim 1, wherein the hydrogenating (c) is conducted in the presence of a hydrogenation catalyst comprising a hydrogenation component and a support.

12. The process of claim 11, wherein the hydrogenation component comprises at least one element or compound thereof selected from Groups 6 to 10 of the Periodic Table of Elements.

13. The process of claim 11, wherein the hydrogenation component comprises palladium or a palladium compound.

14. The process of claim 11, wherein the hydrogenation component comprises about 0.1 wt % to about 10 wt % of the hydrogenation catalyst.

15. The process of claim 11, wherein the hydrogenation component comprises about 0.3 wt % to about 1 wt % of the hydrogenation catalyst.

16. The process of claim 11, wherein the support comprises at least one of aluminum oxide, silica, silicate, aluminosilicate, carbon, and a carbon nanotube.

17. The process of claim 1, wherein at least part of the second reaction product comprising phenol, cyclohexanone, and cyclohexenone is subjected to the hydrogenating (c).

18. The process of claim 1, wherein the second reaction product is separated into a first stream rich in cyclohexanone and cyclohexenone and a second stream rich in phenol, and at least part of the first stream is subjected to the hydrogenating (c).

19. The process of claim 1, wherein at least part of the cyclohexylbenzene in (a) is formed by reacting benzene with hydrogen.

20. The process of claim 1, and further comprising dehydrogenating at least a part of the cyclohexanone from the second reaction product to form phenol.

21. A process for producing phenol, the process comprising:
   (a) reacting benzene with hydrogen to form cyclohexylbenzene;
   (b) oxidizing at least a portion of the cyclohexylbenzene to form a first reaction product comprising cyclohexylbenzene hydroperoxide; and
   (c) cleaving at least a portion of the cyclohexylbenzene hydroperoxide from (a) to form a second reaction product comprising phenol and cyclohexanone,
   wherein at least one of the first and second reaction products comprises at least 0.05 wt % of cyclohexenone and the process further comprises:
   (d) hydrogenating at least a portion of the cyclohexenone to cyclohexanone, wherein at least 50 wt % of the cyclohexenone is hydrogenated.

* * * * *